(12) United States Patent
Lombardo et al.

(10) Patent No.: US 7,266,484 B2
(45) Date of Patent: Sep. 4, 2007

(54) TECHNIQUES FOR EARLY DETECTION OF LOCALIZED EXPOSURE TO AN AGENT ACTIVE ON A BIOLOGICAL POPULATION

(75) Inventors: Joseph S. Lombardo, Annapolis, MD (US); Howard S. Burkom, Baltimore, MD (US); Farzad Mostashari, Brooklyn, NY (US); Eugene Elbert, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 316 days.

(21) Appl. No.: 10/466,459

(22) PCT Filed: Dec. 2, 2002

(86) PCT No.: PCT/US02/38320

§ 371 (c)(1),
(2), (4) Date: Jul. 15, 2003

(87) PCT Pub. No.: WO03/048725

PCT Pub. Date: Jun. 12, 2003

(65) Prior Publication Data
US 2004/0078146 A1 Apr. 22, 2004

Related U.S. Application Data

(60) Provisional application No. 60/337,307, filed on Dec. 4, 2001.

(51) Int. Cl.
*G01N 33/48* (2006.01)
*G01N 31/00* (2006.01)
*G06G 7/48* (2006.01)
*G06G 7/58* (2006.01)

(52) U.S. Cl. .................... 703/11; 702/19; 702/22; 703/11; 703/12

(58) Field of Classification Search ................ None
See application file for complete search history.

(56) References Cited

U.S. PATENT DOCUMENTS 4,469,786 A 9/1984 Garro et al.

(Continued)

OTHER PUBLICATIONS

Tillett et al. Surveillance of outbreaks of waterborne infectious disease: categorizing levels of evidence. Epidemiology and Infection. 1998, vol. 120, pp. 37-42.*

(Continued)

*Primary Examiner*—John S. Brusca
*Assistant Examiner*—Russell S. Negin
(74) *Attorney, Agent, or Firm*—Albert J. Fasulo, II

(57) ABSTRACT

Technique for early detection of localized exposure to an agent active on a biological population include collecting time series for each data type of multiple different data types. The data types are relevant for detecting exposure to the agent. For each data type multiple time series are collected for corresponding multiple locations associated with the data type. Measures of anomalous conditions are generated at the locations for each of the different data types. The measures of anomalous conditions are based on the time series and a temporal model for each data type. Cluster analysis is performed on the measures of anomalous conditions to determine an estimated location, and an estimated extent, of effects from the agent. The techniques allow a surveillance system to avoid diluting the signal of a localized outbreak over too large and area or consuming excessive resources in computing replicas for a matched filter detector.

9 Claims, 10 Drawing Sheets

U.S. PATENT DOCUMENTS

| | | | |
|---|---|---|---|
| 5,911,132 | A | 6/1999 | Sloane |
| 6,070,159 | A | 5/2000 | Wilson et al. |
| 6,134,541 | A | 10/2000 | Castelli et al. |
| 6,154,746 | A | 11/2000 | Berchtold et al. |
| 6,238,337 | B1 | 5/2001 | Kambhatla et al. |
| 6,317,700 | B1 | 11/2001 | Bagne |
| 6,360,184 | B1 | 3/2002 | Jacquez |
| 6,408,300 | B1 | 6/2002 | Bergman et al. |
| 6,457,015 | B1 | 9/2002 | Eastham |
| 6,460,011 | B1 | 10/2002 | Jacquez |
| 2002/0069206 | A1 | 6/2002 | Bergman et al. |
| 2002/0082805 | A1 | 6/2002 | Jacquez |

OTHER PUBLICATIONS

Real LA. Animal choice behavior and the evolution of cognitive architecture. Science vol. 253, 1991, pp. 980-986.*

Newson R et al. Fungal and other spore counts as predictors of admissions for asthma in the Trent region. Occupational and Environmental Medicine, Nov. 2000, vol. 57, pp. 786-792.*

Infantosi A.F.C. et al: "Phase spectral analysis of measles epidemic outbreaks" Medinfo 89. Proceedings of the Sixth Conference on Medical Informatics, Beijing, China and Singapore, Oct. 16-20, 1989 and Dec. 11-15, 1989, pp. 497-501, XP008007972, 1989, Amsterdam, Netherlands.

Nobre, F.F.: "Detecting abnormal patterns in public health surveillance data with probability index function" Medinfo 92. Proceedings of the Seventh World Congress on Medical Informatics, Geneva, Switzerland, Sep. 6-10, 1992, pp. 904-909 vol. 2, XP008007963 199, Amsterdam, Netherlands.

Bailey N.T.J.: "Macro-modeling and prediction of epidemic spread at community level" Mathematic Modelling, 1986, USA vol. 7, No. 5-8, pp. 689-717, XP008007959.

Snacken, R. et al: "The CARE Telematics network for the surveillance of influenza in Europe" Methods of Information in Medicine, Dec. 1995, F.K. Schattauer Verlagsgesellschaft, Germany, vol. 34, No. 5, pp. 518-522, XP008007965.

Nobre F. et al.: "A Monitoring System to Detect Changes in Public Health Surveillance Data," International Journal of Epidemiology, 1994, International Epidemiological Association, vol. 23, No. 2, pp. 408-418.

Quenel, P. et al: "Influenza A and B epidemic criteria based on time-series analysis of health services surveillance data" European Journal of Epidemiology, 1998, Kluwer Academic Publishers, Netherlands, vol. 14, pp. 275-285.

Glass, G.E. et al: "Environmental Risk Factors for Lyme Disease Identified with Geographic Information Systems," American Journal of Public Health, Jul. 1995, vol. 85, No. 7, pp. 944-948.

Co-owned, pending. Related U.S. Appl. No. 10/130,404, filed May 15, 2002, entitled "Method and System for Bio-Surveillance Detector and Alerting," by Lombardo et al.

"Building Communication Networks: International Network for the study and Prevention of Emerging Antimicrobial Resistance" vol. 7, No. 2, Mar.-Apr. 2001 by Richet et al.

International Search Report PCT/US02/38320, mailed May 3, 2004.

* cited by examiner

: Control interface for multiple-source surveillance with Satscan

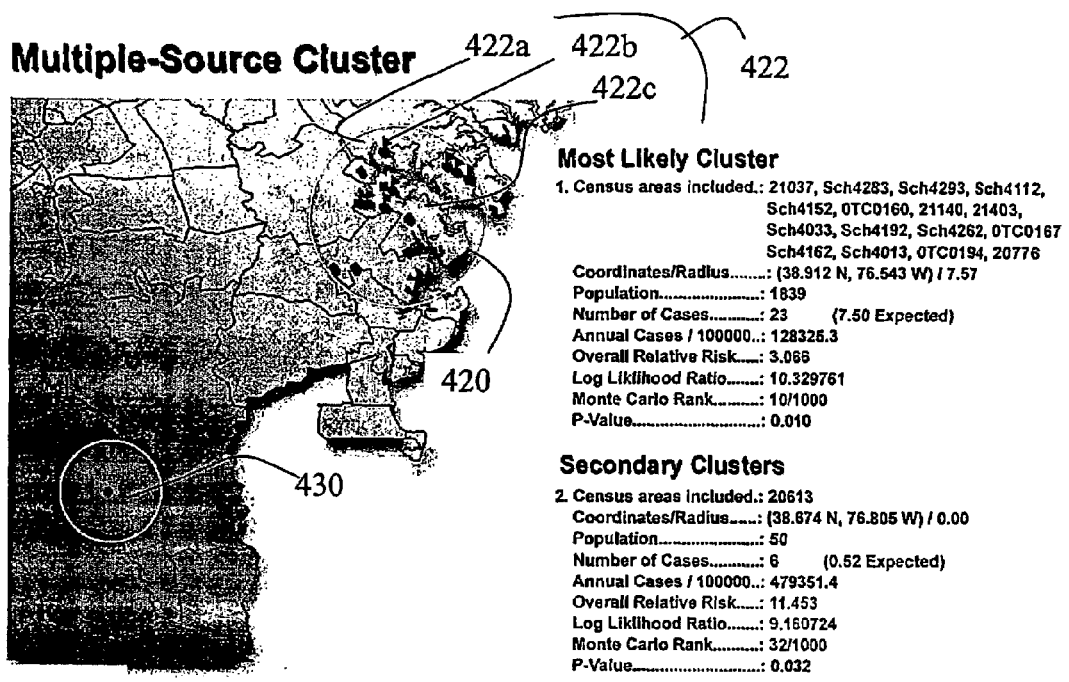
FIG. 4B : Sample output from surveillance combining counts of outpatient visits, OTC anti-flu sales, and school absentees

TECHNIQUES FOR EARLY DETECTION OF LOCALIZED EXPOSURE TO AN AGENT ACTIVE ON A BIOLOGICAL POPULATION

CROSS-REFERENCE TO RELATED APPLICATIONS

This application claims benefit of Provisional Appln. 60/337,307, filed Dec. 4, 2001, the entire contents of which are hereby incorporated by reference as if fully set forth herein, under 35 U.S.C. §119(e). This application also claims benefit as a continuation-in-part of PCT Application Ser. No. PCT/US01/09244, filed Mar. 23, 2001 the entire contents of which are hereby incorporated by reference as if fully set forth herein, under 35 U.S.C. §120.

STATEMENT OF GOVERNMENTAL INTEREST

This invention was made with U.S. Government support under Defense Advanced Research Projects Agency (DARPA) Contract No. MDA972-96-D-0002. The U.S. Government has certain rights in the invention.

BACKGROUND OF THE INVENTION

1. Field of the Invention

The present invention relates to performing surveillance on a biological population for exposure to an agent that acts on members of that population; and in particular to the early detection of localized exposure using cluster analysis on anomalous conditions determined from time series of multiple data types.

2. Description of the Related Art

The past approaches described in this section could be pursued, but are not necessarily approaches that have been previously conceived or pursued. Therefore, unless otherwise indicated herein, the approaches described in this section are not to be considered prior art to the claims in this application merely due to the presence of these approaches in this background section.

Recent history demonstrates that weapons of mass destruction can be built and deployed by almost any individual or group that has intent to cause harm or that is looking chemical and biological agents. These weapons, banned from wartime usage, have nevertheless proliferated in third world countries. Information on the development and deployment of these weapons has become widely available on the Internet. Materials to produce some agents are also readily available. Certain biological agents pose a particularly insidious threat in that a clandestine release into a population may not be noticed during the incubation period of the resultant disease. Yet, concerning agents such as anthrax, once the symptoms are manifested it is no longer possible to treat the victim and high mortality is inevitable. Contagious agents like smallpox or the plague pose even greater threats. Such agents require early identification of an infected population in order to treat the victims and contain a potentially devastating epidemic.

Use of biological weapons therefore poses very serious issues for crisis and consequence management. Various State and local emergency management plans utilize fire, rescue, and law enforcement first responders to provide emergency assistance, to control an incident site, and to collect evidence for criminal prosecution. For clandestine bio-agent releases, the medical community may be the first to see patients present with uncommon diseases. These diseases include small pox, plague, tularemia, anthrax, etc., and have a high mortality rate. In order to institute measures to contain disease outbreaks, public health officials must receive timely reports from agencies and health providers in their jurisdiction. Early warning is key to managing an epidemic and saving lives. However, the first indicators of a bio-terrorist event may be the onset of disease in humans and animals. And professionals from the health care community may not be able to recognize the early signs of diseases that would result from bio-terrorism. Early diagnosis of such diseases is often difficult because the diseases generate only common "flu-like" initial symptoms.

To overcome the obstacles concerning an effective early warning system, improved technology is needed. Information technology and advanced telecommunications can play a major role in improving surveillance for biological and chemical weapons of mass destruction. Information integrated from multiple sources that interface with the health care needs of a community can provide early warning for the onset of an outbreak resulting from terrorist activities. Even seemingly small advances in early warning timing could save a tremendous number of lives.

However, there are significant limitations with previous attempts at constructing early warning bio-surveillance systems. Conventional bio-surveillance focuses on categorical data collected from emergency rooms, clinics, and other healthcare facilities. The detection algorithms in these conventional systems rely on threshold crossing algorithms applied to single streams of data. Such an approach does not make optimal use of available information and cannot detect a bio-terrorist attack until sizeable numbers of infected individuals appear at healthcare facilities.

Further, conventional bio-surveillance is labor-intensive. For an early warning system to be a viable option several processes must be instituted. First, data from multiple agencies that interface with human health, animal health, and agriculture must be collected and forwarded to a central integration facility. In most systems, a human analyst is needed to review all the data received to extract indicators of a bio-terrorist event. If indicators are found, the analyst needs to assemble the knowledge to form an argument. When an argument is sufficiently mature, the analyst must originate alerts to the specific organizations that need to respond to the incident. This form of bio-surveillance requires continuous support, delays alerts and may be cost prohibitive both for the agencies supporting and analyzing the data.

A need exists therefore for automated early warning bio-surveillance detection and alerting system. Such a system should be capable of operating continuously with minimal human intervention, and should exploit the data collection and analysis capabilities of modern information technology and advanced telecommunications.

In one recent approach for a more fully automated early warning system, described in the related PCT application cited above, data from multiple data types indicative of non-specific, flu-like responses to active agents are collected. A background is generated and subtracted from the data to form residuals. The residuals are used with a matched filter to detect exposure of a population to biologically active agents. The matched filter employs replica signals for residuals in the multiple data types based on one or more hypothetical exposure events. The replicas are compared to observed residuals to determine when a match occurs that indicates the likelihood of an actual outbreak similar to the hypothetical event at a given level of significance for a given limit on false alarms. A system based on this recent approach detects an outbreak more rapidly than other approaches that rely on a single data type.

While suitable for many purposes, and offering many advantages over prior approaches, this recent approach also suffers some disadvantages. One disadvantage is that a great deal of processing power is consumed to generate replicas for even a limited region. This consumption inhibits the use of the method over large geographic regions, such as the eastern or western United States.

Another disadvantage is that a larger area is subject to more different phenomena that contribute to variability of the observed data types and thus introduce noise that can mask indications of a localized exposure event. As a consequence, the signal-to-noise ratio (SNR) for the larger area is smaller than the SNR in a smaller area that contains the outbreak. In essence, the signal is diluted over the larger area.

Furthermore, in this recent approach, the background for a particular location is determined using a retinal banding approach that determines the average value of the data at locations around the particular location but excluding the particular location. If the signal encompasses a cluster of several neighboring locations where data are collected, the background computed using this recent approach may contain some of the signal and the computed residual may be smaller than the actual or predicted residual. This can degrade the detection of an actual localized event by the matched filter.

Based on the foregoing description, there is a clear need for an automated early warning bio-surveillance detection and alerting system that can be scaled up to cover larger areas and that does not suffer the disadvantages of the other approaches.

SUMMARY OF THE INVENTION

Techniques are provided for early detection of localized exposure to an agent active on a biological population. The techniques include collecting time series for each data type of multiple different data types. The data types are relevant for detecting exposure to the agent. For each data type, multiple time series are collected for corresponding multiple locations associated with the data type. Measures of anomalous conditions are generated at the locations for each of the different data types. The measures of anomalous conditions are based on the time series and a temporal model for each data type. Cluster analysis is performed on the measures of anomalous conditions to determine an estimated location, and an estimated extent, of effects from the agent.

In various aspects, the techniques include a method, a computer-readable medium, and a system that implement the steps described above.

The techniques allow a surveillance system to more rapidly detect an event by combining signals spread over multiple data types with information about expected characteristics of the signal in those various data types. Furthermore, the techniques allow the surveillance system to avoid diluting the signal of a localized outbreak over too large an analysis area by focusing a detector on a spatial cluster identified by cluster analysis. In addition, the techniques allow the surveillance system to avoid consuming excessive resources in computing an exposure event in multiple source detectors, such as an exposure event associated with a best matched replica in a matched filter detector, by focusing the application of the multiple source detector in the vicinity of the cluster.

BRIEF DESCRIPTION OF THE DRAWINGS

The present invention is illustrated by way of example, and not by way of limitation, in the figures of the accompanying drawings and in which like reference numerals refer to similar elements and in which:

FIG. 4B is a graph that illustrates a resulting cluster in a geographic area and the locations of time series that fall inside the cluster determined during the cluster analysis step of the method of FIG. 1A, according to an embodiment;

FIG. 4C is a graph that illustrates correct cluster detection and false cluster detection probabilities of the cluster analysis step of the method of FIG. 1A, according to an embodiment;

DETAILED DESCRIPTION

A method and apparatus for early detection of localized exposure to an agent active on a biological population are described. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Embodiments of the invention are described below in the context of detecting flu-like symptoms that are shared by several biological agents during early exposure stages. The data types are therefore not specific to any one of those agents. Also the data types comprise time series with a temporal resolution of one day.

However, the invention is not limited to this context. For example, in other embodiments, data types indicative of more specific symptoms of a particular biological agent may be used. Furthermore, in some embodiments data types indicative of exposure to a chemical agent, rather than a biological agent, may be used to alert responsible authorities to a chemical attack. In some embodiments, the data may be available on a finer time scale, such as reports of human health problems accumulated through a 911 emergency reporting system with time resolutions of hours or minutes.

1. Functional Overview

Figure 1A:
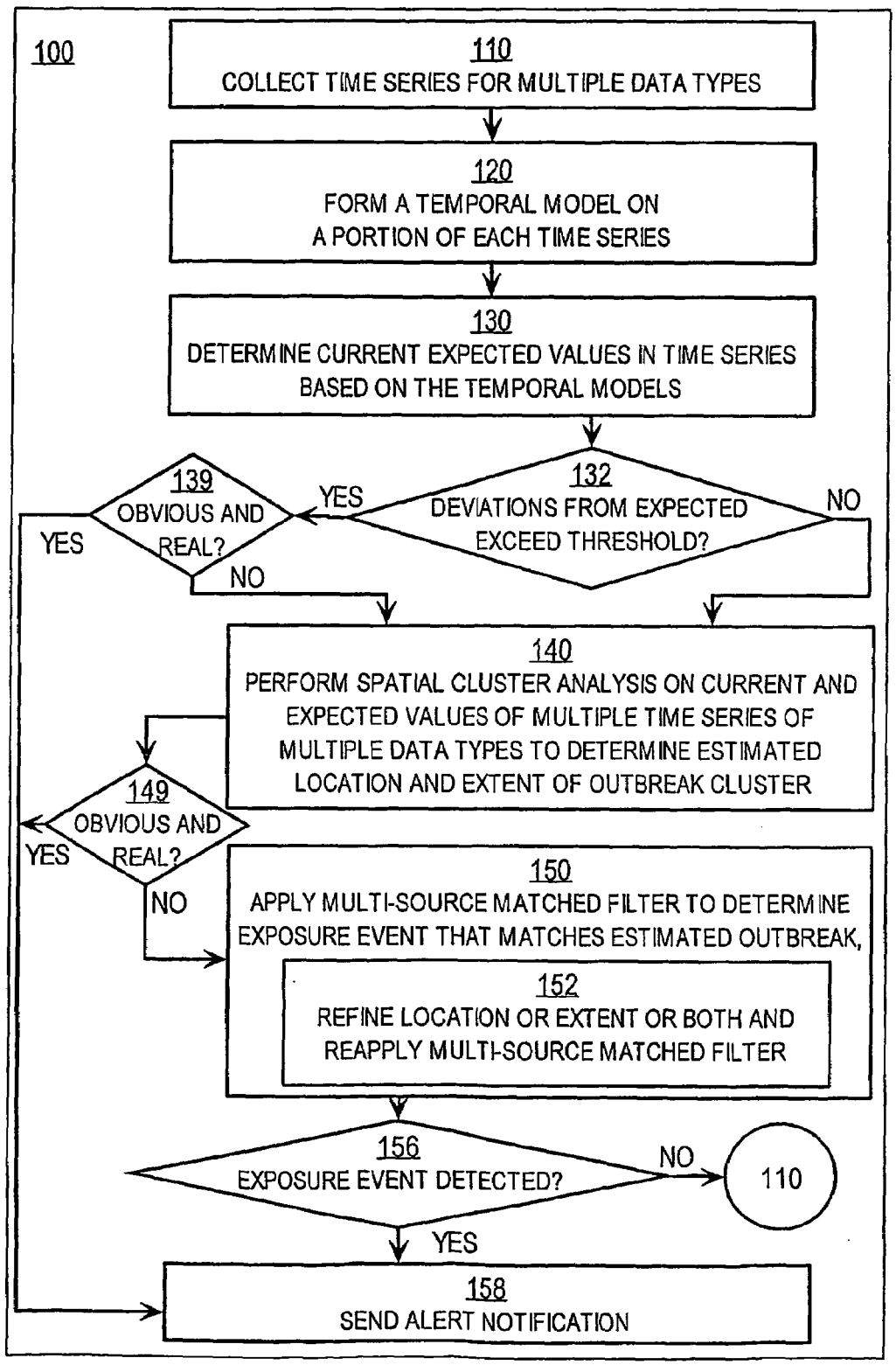
FIG. 1A is a flow chart that illustrates at a high level a method for early detection of localized exposure to an agent active on a biological population, according to an embodiment.

FIG. 1A is a flow chart that illustrates at a high level a method 100 for early detection of localized exposure to an agent active on a biological population, according to an embodiment. Although steps are shown in FIG. 1A in a particular order, for purposes of illustration, in other embodiments the steps may be performed in a different order or overlapping in time.

During step 110, time series data are collected for each of several data types. A deviation that appears in each of several data types is more likely to reflect a real exposure event than a deviation that appears in only one data type. The one data type may be subject to an alternative cause or noise that does not occur in another data type. Therefore it is considered extra useful to collect data from multiple data types in the same region. Data collection of multiple data types for an example embodiment is described in more detail below in sub-section 3.

During step 120, a temporal model is formed for each time series. A different type of temporal model may be formed for each data type. An individual temporal model of the given type is then formed for an individual time series of the associated data type by fitting parameters of the model to the data for a portion of the time series during which it is expected that no exposure event has occurred. Such a portion could be selected from a time that precedes the current time by an amount large compared to the incubation period of the agents of interest.

Forming temporal models for multiple data types for an example embodiment is described in more detail below in sub-section 4. In the example embodiment, the type of temporal model is developed once for each data type, during a research activity that may precede the collection step 110. During the collection step 110, an individual temporal model of the temporal model type is formed by fitting the portion of the time series with the appropriate model type to determine values for any parameters of the model type. In some embodiments, one or more of the model types do not have adjustable parameters that are determined by fitting a portion of the time series; and the same individual model is associated with each time series of the data type.

During step 130, an expected value is determined for the current time for each time series for all the data types. Each expected value is obtained by applying the individual, fitted temporal models to the time series preceding the current time.

In step 132, it is determined whether the actual values at the current time deviate from the expected values by more than a threshold amount. If so, then control passes to steps 139 and beyond to further examine the actual and expected values for this time series (and, possibly, nearby time series) in order to detect an outbreak and determine an associated exposure event. If not, then control passes to step 140 to perform cluster analysis, described in more detail below. It may be that each of 10 adjoining zipcodes gets 1 or 2 additional cases that do not look unusual to any individual temporal detector. In some embodiments, step 132 represents a step taken by a temporal detector.

In step 139, it is determined whether deviations between actual and expected values are real and make obvious the existence of an outbreak caused by an exposure event. Any method known in the art for determining an obvious, real deviation may be used. For example, if the deviation has a size that is several standard deviations of normal variations about the expected value for the data type, and if the other deviations of similar size are detected in adjacent times of the same time series or adjacent locations in other time series, or both, then the deviation may be considered both real and indicative of an outbreak. If it is determined in step 139 that the deviations are obvious and real, then control passes to step 158 to notify authorities of an exposure alert. In some embodiments, step 139 represents a step taken by a deviation-validity-check component of a surveillance system.

It is expected in many cases that deviations from expected values are subtle and are not obviously the result of a real outbreak from an actual exposure event. For example, similar deviations are sometimes observed without a real outbreak from an actual exposure event. An alert based on such deviations would too often result in a false alarm. False alarm rates that are too high undermine the effectiveness of an alerting system. In such cases, control passes to step 140 and beyond to apply more sophisticated detection techniques.

In step 140, spatial cluster analysis is performed on the current deviations at the multiple locations associated with each of the multiple data types. Performing cluster analysis on multiple data types for an example embodiment is described in more detail below in sub-section 5. In some embodiments, step 140 represents a step taken by a spatial-cluster-analyzer component of a surveillance system. Any cluster analysis approach known in the art at the time the surveillance system is built may be used. In typical embodiments, the result of step 140 is a most likely cluster location, cluster spatial size (extent) and signal size (amplitude) inside the cluster, or measure of the likelihood that the cluster is real. Control then passes to step 149 and beyond to determine if the cluster analysis results indicate a real outbreak associated with an actual exposure event.

In step 149, it is determined whether the signal size is real and makes obvious the existence of an outbreak caused by an exposure event. Any method known in the art for determining an obvious, real cluster may be used. If it is determined in step 149 that the cluster amplitude indicates an obvious and real outbreak, then control passes to step 158 to notify authorities of an exposure alert. In some embodiments, step 149 represents a step taken by a cluster-validity-check component of a surveillance system.

It is expected in many cases that the cluster amplitude suggests an outbreak but not does not make it obvious that a real outbreak has occurred. For example, clusters of the same amplitude are sometimes observed in the absence of an outbreak from a real exposure event, so that an alert based on such a cluster has an unacceptably high chance of being a false alarm. In such cases, control passes to step 150 and beyond to apply more sophisticated detection techniques.

In step 150, a multiple data type ("multiple source") detector is used in the vicinity of the cluster in order to determine whether an actual exposure event near the cluster is most likely the cause of deviations from expected values. Any multiple source detector known at the time the system is built may be used. Performing detection on multiple data types for an example embodiment is described in more detail below in sub-section 6. In the embodiments described below, a multiple source, matched filter is used with the deviations to detect an exposure event. In typical embodiments, the result of step 150 is a most likely exposure event location and exposure event time and exposure event significance level. Control then passes to step 156 and beyond to send an alert if the exposure event is likely enough to be real.

In some embodiments, step 150 includes step 152. In step 152, an analysis region is refined and the multiple source detector is applied again. Any method of refining the analysis region from the cluster location and size may be used. In some embodiments, the cluster analysis is run again for finer spatial scale data. For example, school absenteeism data originally reported by school district is replaced by absenteeism data at individual schools in one or more school districts near the exposure event location; and cluster analysis step 140 is run again. Refining the analysis region for an example embodiment is described in more detail below in sub-section 6. In the embodiment described below, the analysis region is refined by running replicas for the matched filter at individual schools or stores, or both, near the exposure event location first computed, instead of at centroids of school districts and store accounting groups.

In step 156, it is determined whether an exposure event is detected with enough significance that false alarm rates are acceptably low. If so, then control passes to step 159 to notify authorities of an exposure alert. If not, then control passes back to step 110 to continue collecting time series data.

In step 158, an exposure alert notification is sent to authorities. Any information of use to the authorities may be included in the alert. For example, the alert includes the time and location and significance of the exposure event detected by the multiple source detector and also includes the current size and extent of the outbreak as determined by the cluster analysis and exposure event.

2. Structural Overview

Figure 1B:
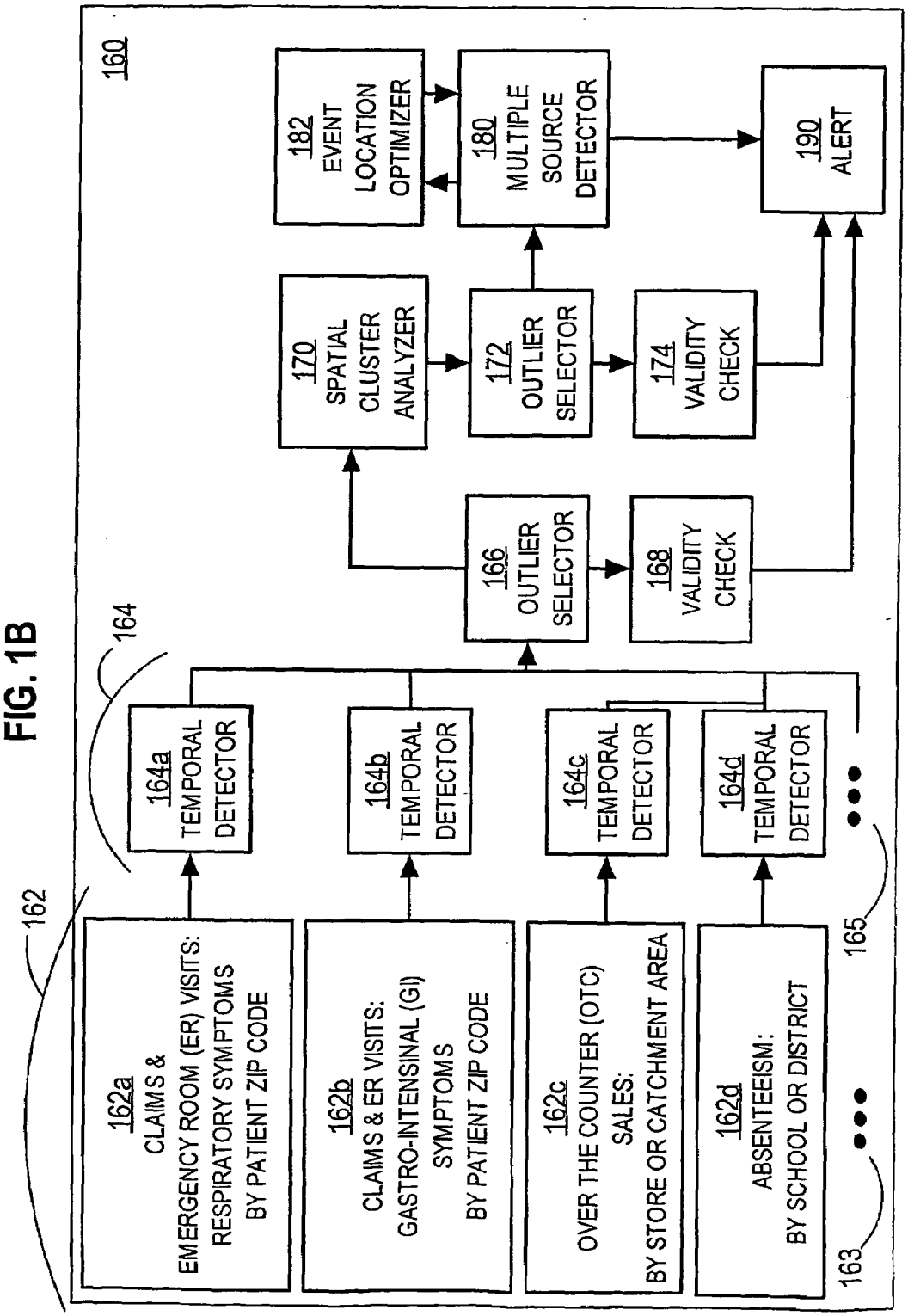
FIG. 1B is a block diagram that illustrates a system that implements the method of FIG. 1A, according to an embodiment.

FIG. 1B is a block diagram that illustrates a system 160 that implements the method of FIG. 1A, according to an embodiment.

System 160 includes data structures 162 that store time series data. Any data structures for storing time series data known in the art may be used. For example, in some embodiments, data structures 162 are one or more database objects in a database system. In some embodiments, data structures are files in a file system.

A variety of data types are stored in time series data structures 162. Data types are selected to indicate population health that may be affected by exposure to the active agents. In a related application cited above, PCT Appln. Ser. No. PCT/US01/09244, filed Mar. 23, 2001 by Lombardo et al. (hereinafter "Lombardo"), a list of multiple different data types are suggested. Based on that list, the following data types are suggested as examples of different data types:

1) high school absentee data—daily absentee and total enrollment figures from public schools in one or more school districts or counties;

2) over the counter (OTC) pharmaceutical sales—sales records for the top 30 products for relief of flu symptoms from drug store chains;

3) emergency room (ER) admissions data—records for admission to hospitals in one or more counties for ER codes that are related to various symptoms of illness;

4) insurance claim billing records—records of insurance claims for insurance codes related to symptoms of illness from a state agency;

5) nursing home illness records—records of employee and resident upper respiratory illnesses from nursing homes in one or more counties; and 6) results of laboratory tests—records of influenza test results from a state health department.

In the illustrated embodiment, time series data structures 162 include time series data structures 162a, 162b, 162c, 162d and ellipses 163 representing other time series data structures, not explicitly depicted. Data structure 162a holds time series data based on insurance claims and ER visits for upper respiratory symptoms segregated by patient zip code. Data structure 162b holds time series data based on insurance claims and ER visits for gastrointestinal (GI) symptoms segregated by patient zip code. Data structure 162c holds time series data based on OTC sales counts segregated by group of stores in a catchment area or by individual store. Data structure 162d holds time series data based on absenteeism (count or percent) segregated by school or school district or county. A location is associated with each time series. Time series data that represents an area, such as a county or zip code, is considered to occupy a location given by a representative location in the area represented, such as a centroid of the area represented. More details on collecting time series data is provided below in sub-section 3. In other embodiments, other data types are used.

The system 160 includes multiple components called temporal detectors 164. Each temporal detector 164, as well as other components depicted in FIG. 1B, may be a separate process or part of a larger process; each component may run on a separate processor dedicated to the process or may share time on the same processor with one or more other processes.

The time series data from data structures 162 are fed into temporal detectors 164. A different temporal detector may be used for different time series. The temporal detectors 164 perform at least one of the steps 120, 130 depicted in FIG. 1A for determining the expected and actual values of the time series at the current time. In the illustrated embodiment, time series data from data structure 162a is input to temporal detector 164a, time series data from data structure 162b is input to temporal detector 164b, time series data from data structure 162c is input to temporal detector 164ca, time series data from data structure 162d is input to temporal detector 164d, and time series data from data structures represented by ellipsis 163 are input to temporal detectors represented by ellipsis 165. More details on the temporal detectors are provided below in sub-section 4.

The system 160 includes components called an outlier selector 166, a validity check 168, and an alert 190. Anomalous conditions detected by one or more of temporal detectors 164, based on the expected and actual values for the current time, are input to outlier selector 166. The outlier selector 166 selects any pair of expected and actual values that represents a deviation that is unusually large, such as a deviation of four standard deviations or more. Any such pair is input to the validity check 168 to determine whether the deviation is real, or is due to noise or other error in the data. If the deviation is determined to be real, data is sent to alert component 190 to notify authorities of the deviation. The components 166, 168 perform the function of step 139 in FIG. IA.

The system 160 includes a component called a spatial cluster analyzer 170. The spatial cluster analyzer 170 performs step 140 depicted in FIG. 1A for determining the most likely one or more clusters based on the expected and actual values of the time series at the current time. In the illustrated embodiment, anomalous conditions represented by expected and actual values at the current time for the multiple time series at multiple locations are input to spatial cluster analyzer 170. Data not selected by the outlier selector 166, is input to the spatial cluster analyzer 170. In some embodiments, outliers that could not be determined to be real are also input to spatial cluster analyzer 170; in other embodiments, outliers that could not be determined to be real are rejected and not used in further processing. More details on the spatial cluster analyzer 170 are provided below in sub-section 5.

The system 160 includes a second set of components called outlier selector 172 and a validity check 174. Significant clusters detected by the spatial cluster analyzer 170 are input to outlier selector 172. The outlier selector 172 selects any cluster that has an unusually large significance, such as a significance level of 0.05 or less. Any such cluster is input to the validity check 174 to determine whether the cluster is real, or is due to noise or other error in the data. If the cluster is determined to be real, data is sent to alert component 190 to notify authorities of the cluster. The components 172, 174 perform the function of step 149 in FIG. 1A.

The system 160 includes a component called a multiple source detector 180. The multiple source detector 180 performs at least one of steps 150, 156 depicted in FIG. 1A for determining an estimated location and time of an exposure event that leads to the observed cluster of anomalous conditions. One or more clusters not selected by the outlier selector 172, are input to the multiple source detector 180. In some embodiments, clusters that could not be determined to be real outbreaks are also input to multiple source detector 180; in other embodiments, clusters that could not be determined to be real are rejected and not used in further processing. If an exposure event is detected that is likely enough to be real, then data is sent to the alert component 190. More details on the multiple source detector 180 are provided below in sub-section 6.

The system 160 includes a component called event location optimizer 182. The event location optimizer 182 performs step 152 depicted in FIG. 1A for refining an analysis area for determining a modified location and time of the exposure event. More details on the event location optimizer 182 are provided below in sub-section 6.

3. Collecting Time Series Data

Figure 2:
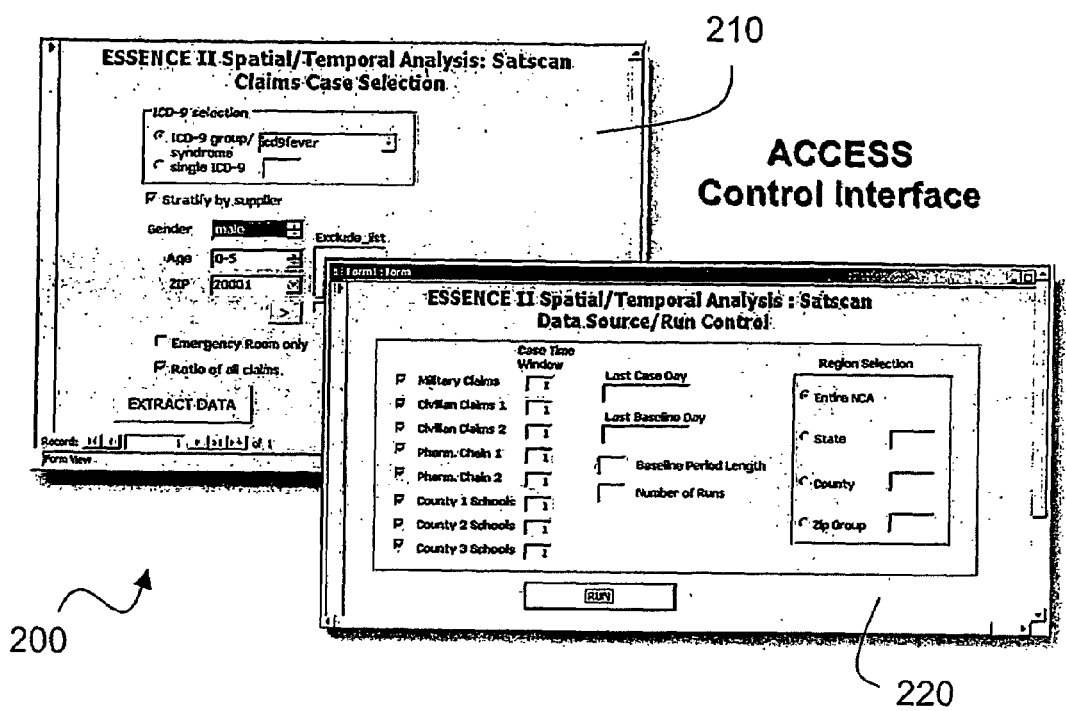
FIG. 2 is a screen shot that illustrates a control interface for collecting data for the system of FIG. 1B during the data collection step of the method depicted in FIG. 1A, according to an embodiment.

FIG. 2 is a screen shot 200 that illustrates a control interface for collecting data for the system of FIG. 1B during the data collection step 110 of the method 100 depicted in FIG. 1A, according to an embodiment. FIG. 2 shows the control form and the data specification form for outpatient visits as screen shot 200. According to this embodiment, time series data are stored in an ACCESS database available from Microsoft Corporation; thus, the data structures 162 are data structures in a Microsoft ACCESS database.

The screen shot 200 includes two windows 210, 220. A first window 210 is used to select the types of claims to form at least one of the time series to be used by the system 160. In the illustrated embodiment, window 210 is used to select insurance claims and ER visits by males five years of age and younger in zip code 2001, who show a fever; the data is reported as a ratio of all claims. A second window 220 is used to select all the time series to be used by the system 160. In the illustrated embodiment, window 220 is used to select military ER claims, two types of civilian claims (insurance and ER), OTC sales by two drug store chains, and school absentee data in three counties.

Thus, in the illustrated embodiment, time series of several different data types are combined to detect an outbreak of symptoms and to determine an exposure event that leads to the outbreak. This ACCESS-based system allows analysts to include or exclude data sources, vary time windows separately for different data sources, censor data from subsets of individual providers or sub-regions, adjust the background computation method, and run retrospective and/or simulated studies.

4. Temporal Models Specific to Data Type

Temporal models used in data-type specific temporal detectors 164 of the illustrated embodiment fall into two main categories. One category of temporal models includes temporal pattern models; the other category includes process control models. In other embodiments, other temporal models or spatial models or combined models for one or more data types may be used.

4.1 Temporal Pattern Example

Temporal pattern models characterize specific features of the time series, such as a seasonal or weekly pattern. These models include general linear mixed models that predict a value at a next time based on a linear combination of observable parameters at present or past times. Models in this category include Poisson, multivariate, linear, logistic regression, and autoregressive models, all well known in the art.

Figure 3A:
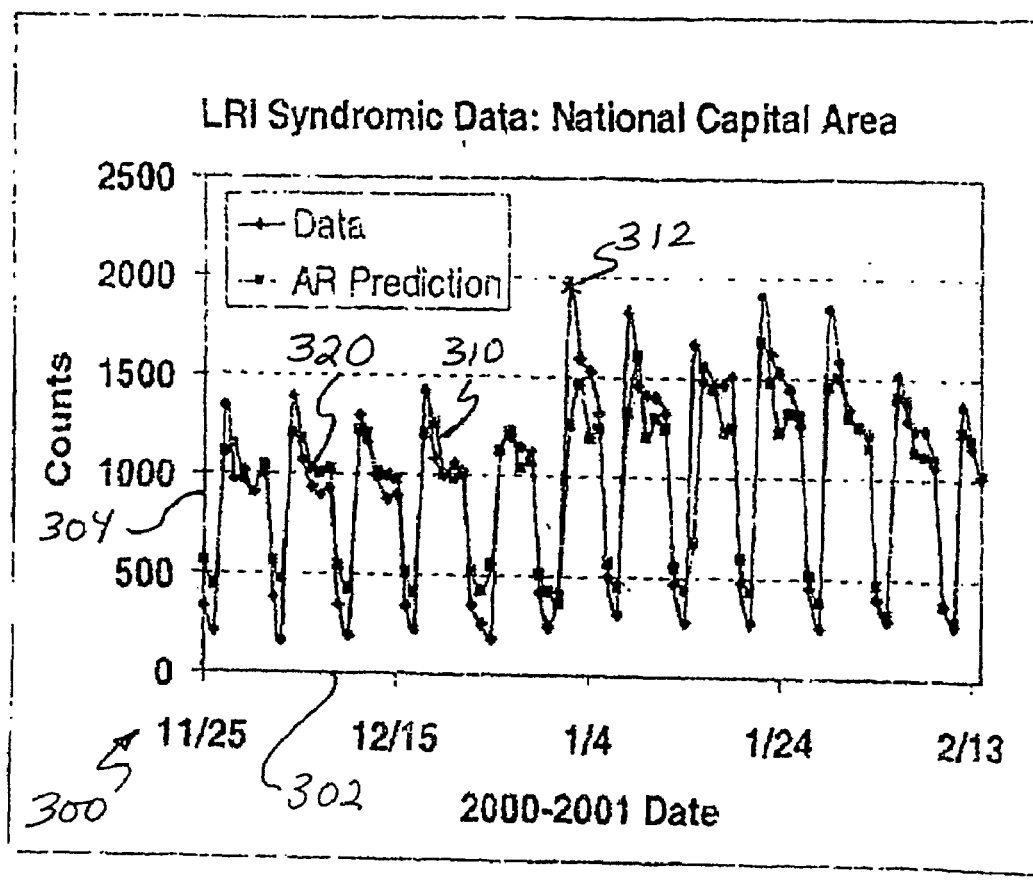
FIG. 3A is a graph that illustrates a time series of data from one data type and expected values for the time series based on an autoregressive temporal model during the temporal modeling step of the method of FIG. 1A, according to an embodiment.

FIG. 3A is a graph 300 that illustrates a time series of data from one data type and expected values for the time series based on an autoregressive temporal model during the temporal modeling step 120 of the method 100 of FIG. 1A, according to an embodiment. According to this autoregressive model, the predicted value "Y" of a time series at time "t", represented by the symbol "Yt" is given by Equation 1a:

$$Yt = Xt*b + Vt \tag{1a}$$

where Xt is a value of a function "X" of time at time t, b is a deterministic correction factor based on such factors as day of the week or time relative to a holiday, among others, and Vt is a deviation "V" at time t. The deviation Vt is a function of a random error term and deviations observed at several preceding times, as given by Equation 1b:

$$Vt = \epsilon t - \phi_1 * Vt-1 - \phi_2 * Vt-2 - \phi_3 * Vt-3 - \ldots - \phi_m * Vt-m \tag{1b}$$

where $\epsilon t$ is normally distributed with a mean of zero and a variance of $\sigma^2$, and the coefficients $\phi$ are determined based on fitting the model to data that does not contain a localized exposure event, such as an accident or hostile attack. This autoregressive model is well known in the art and can be applied using commercially available software such as SAS.

In an illustrated embodiment, this autoregressive model has been applied using SAS software to model time series of insurance claims indicating various symptoms (such as upper respiratory infection symptoms, lower respiratory infection symptoms, and gastro-intestinal symptoms), and OTC sales. The term Xt*b has been used to correct for weekend effects, holiday effects, post-holiday effects, and seasonal effects. For data with more than 10 counts per day, the degree of fit, measured by the statistic $R^2$, is good, indicating a good fit to the data.

FIG. 3A depicts a graph 300 of two curves 310, 320 representing two time series. The horizontal axis 302 is date indicated by month/day for a time interval from Nov. 25, 2000 through Feb. 13, 2001. The vertical axis 304 is the count of claims filed that report lower respiratory infection (LRI) symptoms for an analysis region in the national capital area. Curve 310 represents a time series of observations. These observations are based on actual claims with an artificial signal added after Jan. 1, 2001 to represent an exposure event on Jan. 1, 2001. Curve 320 represents a time series of predictions by the autoregressive model. The data curve 310 shows a weekly temporal pattern. There are few counts on two weekend days each week, when many offices are closed, and extra counts on Monday, when the weekend cases are added to the reports made that day. The data curve 310 also shows a seasonal temporal pattern. The counts increase in January compared to November and December.

The prediction curve 320 tracks the claims curve 310 quite well including the weekly and seasonal patterns. However, the prediction curve is substantially below the data curve 310 for Monday peaks between dates January 4 and about January 31 when the artificial signal was effective. The asterisk marks point 312 where the data curve 310 deviates sufficiently from the prediction curve 320 to cross a threshold used to detect anomalous conditions.

4.2 Process Control Example

Process control models are used to detect small deviations in the tolerances of manufactured items. Models in this category include cumulative summation (CUSUM) and exponential weighted moving average (EWMA) models, well known in the art.

Figure 3B:
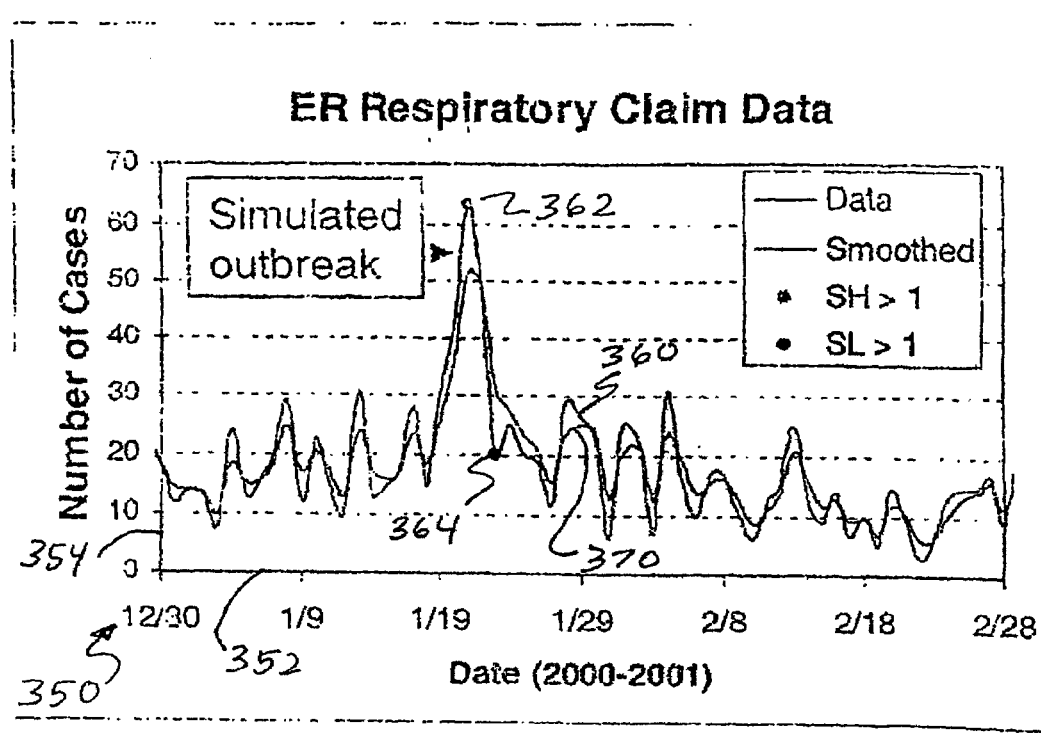
FIG. 3B is a graph that illustrates a time series of data from another data type and expected values for the time series based on a process control temporal model during the temporal modeling step of the method of FIG. 1A, according to an embodiment.

FIG. 3B is a graph 350 that illustrates a time series of data from another data type and expected values for the time series based on a process control temporal model during the temporal modeling step 120 of the method 100 of FIG. 1A, according to an embodiment. According to this CUSUM model, a smoothed value "S" of a time series at time "t", represented by the symbol "St" is obtained from a data stream of observations "O" at one or more previous times. An example of exponential smoothing is given by Equation 2a:

$$St = \omega * Ot-1 + (1-\omega) * St-1 \quad (2a)$$

where ω has a value between zero and 1. The deviations between St and Ot for several values of t are used to derive a root mean variance $\sigma_t$, and the normalized deviation "Z" at time t, represented by the symbol "Zt" is obtained using Equation 2b:

$$Zt = (Ot - St)/\sigma_t \quad (2b)$$

The cumulative sums "$S_H$" and "$S_L$" are computed according to Equations 2c and 2d, respectively:

$$S_H = \text{maximum of 0 and } (Zt-k) + \text{old } S_H \quad (2c)$$

$$S_L = \text{maximum of 0 and } (-Zt-k) + \text{old } S_L \quad (2d)$$

The values of $S_H$ and $S_L$ are then compared to a threshold "h" indicating significant deviations. The values of ω, h and k, and a method for estimating $\sigma_t$, are tuned using test data to provide the earliest reliable alerts.

In the illustrated embodiment, this CUSUM method is used as a temporal model with emergency room (ER) visits which show less drastic temporal patterns than are shown by insurance claims. When the CUSUM method was tuned to theses data, the value of the threshold h was determined to be 1.

FIG. 3B depicts a graph 350 of two curves 360, 370 representing two time series. The horizontal axis 352 is date indicated by month/day for a time interval from Dec. 30, 2000 through Feb. 28, 2001. The vertical axis 354 is the count of respiratory cases in ERs for an analysis region in the national capital area. Curve 360 represents a time series of observations. These observations are based on actual cases with an artificial signal added after Jan. 20, 2001 to represent an exposure event on Jan. 20, 2001. Curve 370 represents a time series of smoothed values using Equation 2a. Point 362 marks a time when the value of $S_H$ exceeds the threshold 1 and Point 364 marks a time when the value of $S_L$ exceeds the threshold 1. Thus points 362 and 364 represent anomalous conditions for ER respiratory cases.

5. Cluster Analysis

Cluster analysis is a well-known technique for finding spatial concentrations in values for a single data type. For example, a method of cluster analysis is described in "A spatial scan statistic," M. Kulldorff, *Communications in Statistics: Theory and Methods*, v26, 1997, pp1481-1496, and "Spatial scan statistics: models, calculations, and applications," by M. Kulldorff, *Scan Statistics and Applications*, J. Glaz, Ed., Birkhauser, Boston, 1999, pp 303-322 (hereinafter, collectively referenced as Kulldorff). Kulldorff presents a generalized spatial scan statistic which can be prepared from data of disease occurrence in a population for use in determining the location and extent of circles that enclose the most likely clusters of the disease. The generalized scan statistic is based on a pair of values: 1) an actual count for occurrences of the disease in an area; and 2) an expected value based on the population in the area and a rate of occurrence of the disease in the general population. Software (called "Satscan") based on the cluster analysis of Kulldorff is available at the website of the National Cancer Institute.

Figure 4A:
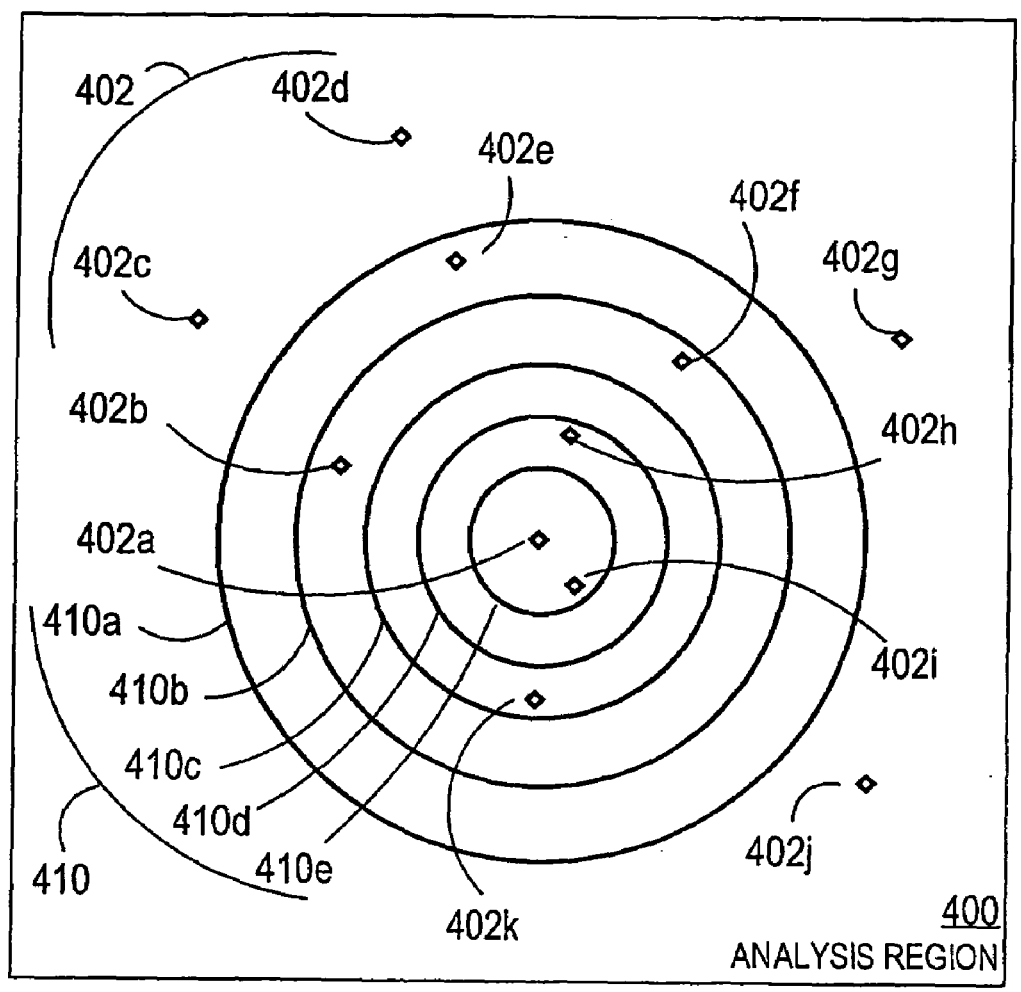
FIG. 4A is a block diagram that illustrates a spatial relationship between locations associated with time series and circular areas used to form candidate clusters during cluster analysis step of the method of FIG. 1A, according to an embodiment.

FIG. 4A is a block diagram that illustrates a spatial relationship between locations associated with time series and circular areas used to form candidate clusters during cluster analysis step 140 of the method 100 of FIG. 1A, according to an embodiment. The analysis region 400 includes locations 402 for multiple time series of data from one or more data types. Locations 402 include locations 402a, 402b, 402c, 402d, 402e, 402f, 402g, 402h, 402i, 402j, 402k, among others, not shown. A time series of data associated with an area is represented by a centroid or other representative location for the area. A series of concentric candidate circles are constructed around each location in the analysis region 400 to determine whether a cluster might be centered on that location. Projecting the circles in a time dimension perpendicular to the analysis region 400 forms corresponding "cylinders". In the illustrated example, candidate circles 410 are centered on location 402a. Candidate circles 410 include concentric candidate circles 410a, 410b, 410c, 410d, 410e, among others, not shown. For each candidate circle, a likelihood ratio of event counts inside a corresponding cylinder relative to the event counts in the entire region is determined, within some time and space limits. The most likely spatial cluster is then the one or more areas whose representative locations are within the circular base of the cylinder with the maximum likelihood ratio. For example, if the cylinder with the maximum likelihood ratio has base circle 410d, then the areas represented by locations 402a, 402h and 402i combine to form the most likely cluster.

According to embodiments of the present invention, unlike Kulldorff, the data at the locations 402 can be different data types. For some data types there may be no known rate of occurrence in the general population or no known underlying population. The data types may represent overlapping areas, such as counties and store catchment areas. The data types are combined in the cluster analysis by presenting both the observed value at each location and the predicted value from the temporal model. In embodiments that use software based on the Kulldorff approach, if two data types have the same centroids, or other representative locations, then one or both of the data types are associated with a different representative location so that no two locations provided to the software have the same location. Typically the different location is spatially close to the original location.

Given a subdivision of a surveillance region into sub-regions, the Satscan software is designed to find one or more clusters of the sub-regions where combined data counts are most unlikely due to normal fluctuations, and designed to evaluate the significance of these clusters, e.g., by estimating how unlikely the counts in the clusters are.

Candidate clusters are formed by considering each of a family of circles centered at each of a set of grid points—often taken as the full set of sub-region centroids. A candidate cluster comprises sub-regions whose centroids lie in the associated circle. For each grid point, candidate cluster sizes range from a single sub-region up to a preset maximum fraction of the total case count N. In Satscan, a statistic called the likelihood ratio (LR) is computed for each candidate cluster, as given by Equation 3:

$$LR(J) = O(J)/E(J)^{O(J)} * \{[N-O(J)]/[N-E(J)]\}^{[N-O(J)]} \qquad (3)$$

where J refers to the set of sub-regions whose centroids lie in a candidate circle, O(J) is the sum of the observed counts in the sub-regions included in J, E(J) is the sum of the expected counts in the sub-regions included in J, and N is the total number of cases in the region.

The cluster J* with the larges value of LR over the sets J obtained from all grid centers and all radii up to a fixed limit is then the maximum likelihood cluster. Satscan determines a p-value estimate for the statistical significance of this cluster empirically by ranking the value of LR(J*) against other maximum likelihood ratios, each calculated similarly from a random sample of the N cases based on the expected spatial distribution. The p-value indicates the probability that the count is observed by chance due to normal fluctuations. Once a set of sub-regions is associated with a maximal cluster, Satscan chooses secondary clusters and assigns them significance levels from the successively remaining sub-regions.

In illustrated embodiments, Satscan is adapted to work with different data types. In the conventional use of Satscan, expected values for the sub-regions are calculated from the respective populations, assuming uniform spatial incidence. However, counts from many of the different data sources are not population-based. For example, the distribution of insurance claim data depends on factors such as the distribution of eligible consumers and participating care providers and day of the week. We have derived expected counts from temporal modeling of individual sub-region counts and from recent data history. A common technique is to use the spatial distribution of counts from a baseline interval chosen long enough to represent the entire region yet recent enough to represent temporal trends.

For combining counts from multiple sources, different data types were treated as covariates so that Satscan could operate on them directly. Expected values for each source are calculated from source-specific modeling. Once expected values are computed, covariate observed and expected counts are summed and the likelihood ratio statistic is computed. This approach has been applied to multiple sources of medical data treated separately, to absentee counts from different counties normalized by county schedule, and to OTC sales from separate store chains. This approach allows the mixture of data organized by such variables as patient residence zip-code, provider location, and store or school address. When adding a new data source, a new covariate number is assigned and the new locations are appended to the aggregate file of spatial coordinates, provided only that exact coordinates are not repeated and that each zip-code or site has a unique identifying string. Expected and observed counts for the new source are then tabulated and included as covariate counts along with counts of the remaining data sources. The spatial clustering includes locations of all the various data sources.

Detailed data analysis is often desirable before a new data source is included in the surveillance clustering. Without such analysis, applying a scan statistic may produce spurious clusters that can mask the space-time interaction of interest. The general principle is to include the most "signal," or cases of interest, with the least "noise." Specific analysis issues are the selection of the outcome variable and the method for choosing the expected spatial distribution. Choice of an outcome variable is important in the use of diagnosis counts for clustering. For medical data, syndromic surveillance is used, e.g., monitoring counts of outpatient visits by diagnoses falling in any of several syndrome groups.

To illustrate these principles, an embodiment appropriate for a particular surveillance system is herein described. The U.S. Department of Defense Global Emerging Infections System (DoD-GEIS) has developed the Electronic Surveillance System for the Early Notification of Community-based Epidemics (ESSENCE) to enable outbreak alerting using syndromic surveillance. ESSENCE monitors over 100 primary care and emergency clinics in the National Capital Area (NCA) and, collects approximately 100,000 claims per day several times daily from military treatment facilities worldwide. ESSENCE II, an extension of this system, collects both civilian and military data in the NCA, plus less specific but potentially timelier indicators, such as records of over-the-counter (OTC) remedy sales and school absenteeism. Principal objectives of ESSENCE II are the early identification, characterization, and tracking of disease outbreaks.

For the ESSENCE project, seven syndrome groups were chosen by DoD-GEIS for surveillance: respiratory, gastrointestinal, fever, dermatologic infectious, dermatologic hemorrhagic, neurologic, and coma. ESSENCE increments the count for a syndrome group each time a diagnosis code falls in the corresponding list.

The spatial and temporal behavior of the various syndrome group counts, especially during cold season, are examined to refine the syndrome groups and subgroups for more sensitive, specific clustering. To reduce noisy temporal behavior at the local level that can lead to excessive clustering, each source of data is evaluated before being included in the analysis. For example, absentee counts from a school that often skips reporting or whose counts are especially erratic would be excluded. For OTC sale data, counts are usually restricted to sales of influenza or diarrhea remedies.

5.1 Application to Real Cases

Combinations of data sources for both retrospective studies of known outbreaks and surveillance of high-profile events of concern to local public health authorities have been processed. FIG. 4B is a representative portion of an output file. FIG. 4B is a graph that illustrates a resulting cluster in a geographic area and the locations of time series that fall inside the cluster determined during the cluster analysis step 140 of the method 100 of FIG. 1A, according to an embodiment. A primary cluster has a location represented by the center of the circle 420 and an extent given by the sub-regions, which have representative locations within the circle 420. A radius of circle 420 may be used as a proxy for the extent of the cluster. The locations of time series are shown as solid symbols 422 inside the circle 420.

Different symbol shapes represent different data types. For example, school symbols, like school symbol having a circular base 422a and triangular flag 422b, represent locations of time series of school absenteeism data type, and diamonds, like symbol 422c, represent locations of time series of pharmacy sales data type. Zip code centroids representing patient residential zipcodes in medical data were not plotted to avoid a cluttered figure. Note that clusters may include sites from any combination of the included data sources.

A secondary cluster is associated with one time series at the center of the circle 430.

5.2 Simulations

In the absence of substantial disease outbreaks to demonstrate the advantage of clustering with multiple data sources, simulations are used to examine the potential advantage in the event of a localized attack. A purely spatial Monte Carlo simulation is here described as an example.

For a particular data source, for example, for counts of claims from the respiratory syndrome, expected spatial probabilities for the sub-regions (e.g., patient zip-codes) in the surveillance regions are assumed. The clusters produced using the scan statistic with many repetitions of the following procedure are examined.

1) For a set of background cases, compute a spatial case distribution with a multinomial random draw based on expected spatial probabilities.
2) For a test signal, choose an outbreak epicenter, e.g., an exposure event, in the surveillance region for each test background. Compute a signal probability distribution over the sub-regions, which decays exponentially with the distance from the epicenter. The signal is then a small number of additional cases chosen from this distribution with another multinomial draw.
3) Add the background and signal cases and find the maximum likelihood clusters with a spatial scan statistic.

For each of these clustering attempts, it is determined, for a threshold value "T", in what fraction of all runs is there a computed cluster, containing the epicenter, whose scan statistic exceeds T, and in what fraction is there a computed false cluster whose scan statistic exceeds T. By varying this threshold over the values obtained for computed clusters, a curve is obtained, which is similar to a receiver operating characteristic (ROC) curve that plots the probability of finding the outbreak versus the probability of a false cluster. A graph can be plotted that illustrates correct cluster detection and false cluster detection probabilities of the cluster analysis step of the method of FIG. 1A, according to an embodiment. On the graph, the horizontal axis represents the probability of detecting a false cluster; and the vertical axis represents the probability of detecting a correct cluster that includes the epicenter.

In exemplary cases that can be graphed as described above, the number of outbreak cases is 10% of the number of background cases. A first curve and a second curve are computed by clustering with respiratory claims alone, and OTC anti-flu sales alone, respectively. A third curve is computed by clustering with both data sources. For reasonable detection probabilities, a substantial gain is evident when the sources are combined. For example, at a correct cluster detection probability of 0.6, a false cluster detection probability is about 0.5 using one data type (first or second curves) and about 0.2 using both data types (third curve), a reduction of false clusters by a factor of about 2.5 if both data types are combined.

This technique has several applications. It may be used to assess the marginal surveillance value of a single data source or to check for robustness of the clustering method as the spatial case distribution evolves. It may also be used to compare the performance of the likelihood ratio statistic used in Satscan to other possible scan statistics used in other embodiments, including methods based on contingency tables.

In the illustrated embodiment, disparate sources are treated as covariates whose counts and expected values are summed for the log likelihood ratio. In other embodiments other approaches may be taken. For example the likelihood ratios may be computed separately for disparate sources and then their logarithms may be summed. Preliminary tests suggest that this statistic can prevent one noisy source from masking a signal in another; however, this statistic may lose power to detect a faint signal with traces in all sources. In other embodiments the counts and expected values are weighted by weights determined any of several ways known in the art, or the counts are normalized by variance of the data in the data type.

It is expected that, using these techniques, increases in early outbreak alerting capability can be achieved as the number of data sources and promptness of data reporting increase.

6. Matched Filter Detector Using Multiple Data Types

Clusters identified by Satscan or by the modified methods described above should be understood as approximate locations of concentrated data counts that may indicate an outbreak of disease. The statistical significance and persistence of these clusters should be used to evaluate their importance. They are also valuable as cues for and corroboration of other surveillance measures, such as multi source matched filters described in Lombardo.

As described in Lombardo, replica time series are generated in the appropriate data type for one or more locations based on modeling the effects of one or more hypothetical exposure events (epicenters). According to some embodiments, the hypothetical exposure events are centered at or near the center of the cluster, and replica time series are generated for locations inside the cluster where data are available. Time-domain covariance techniques are applied to seek a likely match between the replica and the data at time of the matching exposure event. The hypothetical event that produces the most likely match is taken as the most likely event. If the significance of the match is high enough, authorities are alerted. The alert includes at least some of the time and location of the most likely event and the significance of the match and perhaps, the location and extent of the cluster.

By confining the matched filter detector to areas in the vicinity of the cluster, substantial computational resources and response time are saved. This aids in obtaining the earliest possible detection of an exposure event.

In some embodiments, the most likely event is used to refine the analysis area, and the matched filter is reapplied. For example, computed relative risks of individual subregions in or near the candidate cluster may be used to exclude or annex subregions to obtain the next cluster candidate, subject to spatial restrictions. In another embodiment, if the best match is not at a time series location at the center of the cluster, where the exposure event is located, then a new exposure event, and associated replicas, are generated, centered on the area that gave the best match in the previous round.

In some embodiments, obtaining a cluster of low significance level is used to focus attention on the cluster. Authorities may be advised that an outbreak is possible and more analysis is required. In some embodiments, the data used to define a maximum likelihood cluster are reviewed and time series of marginal quality are dropped out, and the cluster analysis is run again.

Thus the analysis area and extent are refined to more precisely locate and time the event and obtain significant matches.

Figure 5A:
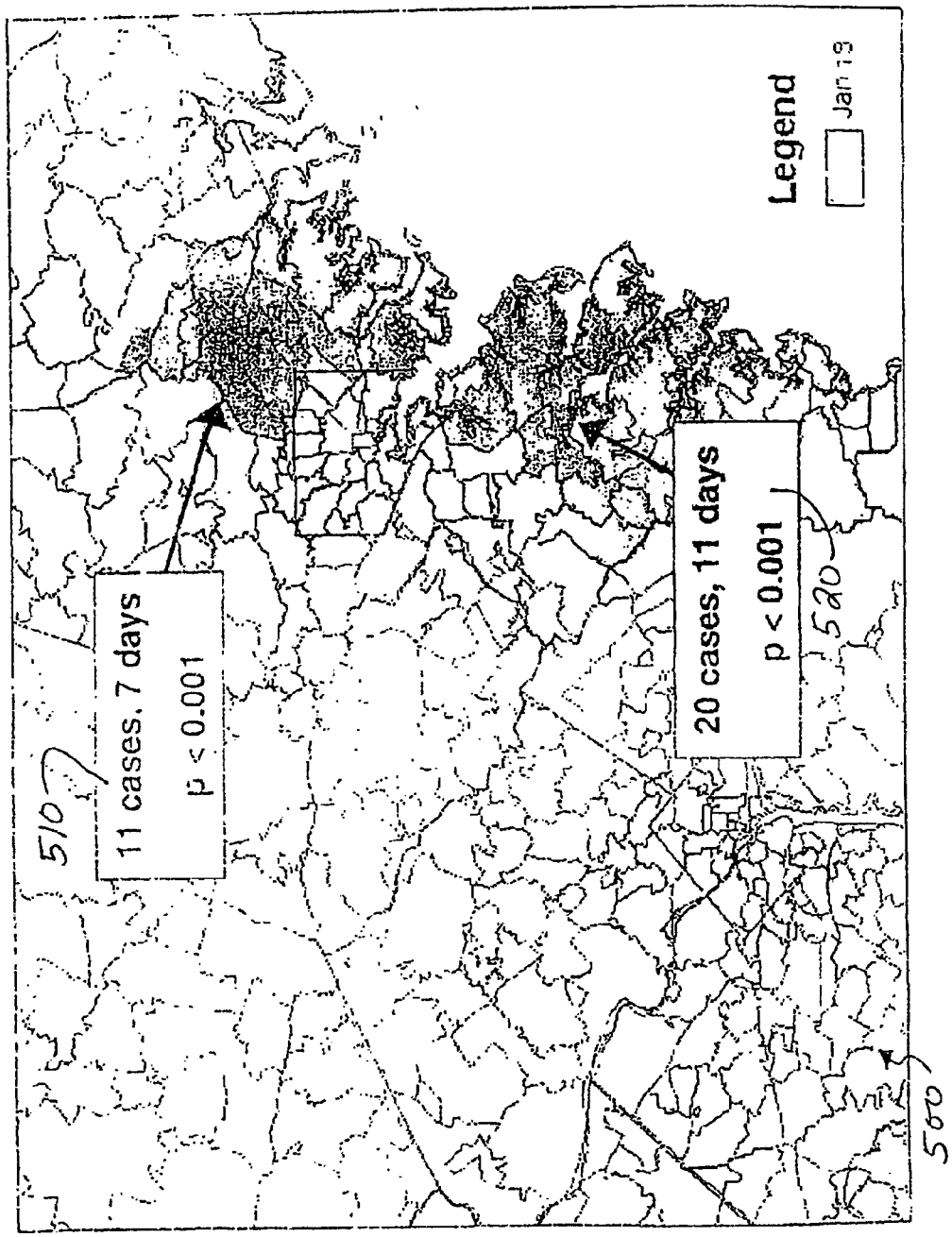
FIG. 5A is a graph that illustrates an example outbreak detection that results from applying the method of FIG. 1A at one date during the time series, according to an embodiment.

FIG. 5A is a graph 500 that illustrates an example outbreak detection that results from applying the method of FIG. 1A at one date during the time series, according to an embodiment. Graph 500 shows a map of sub-regions and two areas where significant outbreaks are detected as of Jan. 18, 2001. One outbreak, indicated by box 510, is associated with 11 cases in 7 days; another outbreak, indicated by box 520, is associated with 20 cases in 11 days. The probability that such outbreaks would be caused by random errors of normal variability is less than 0.001 in both cases; thus the outbreaks are highly significant. .]These data are from a retrospective study where an epidemiologist indicated that a scarlet fever outbreak had occurred. Our outcome variable in each time series was the number of cases of diagnosis code 034, scarlet fever, or 034.1, strep throat due to scarlet fever. Such cases are relatively rare, so case counts were compared to the population-based incidence.

Figure 5B:
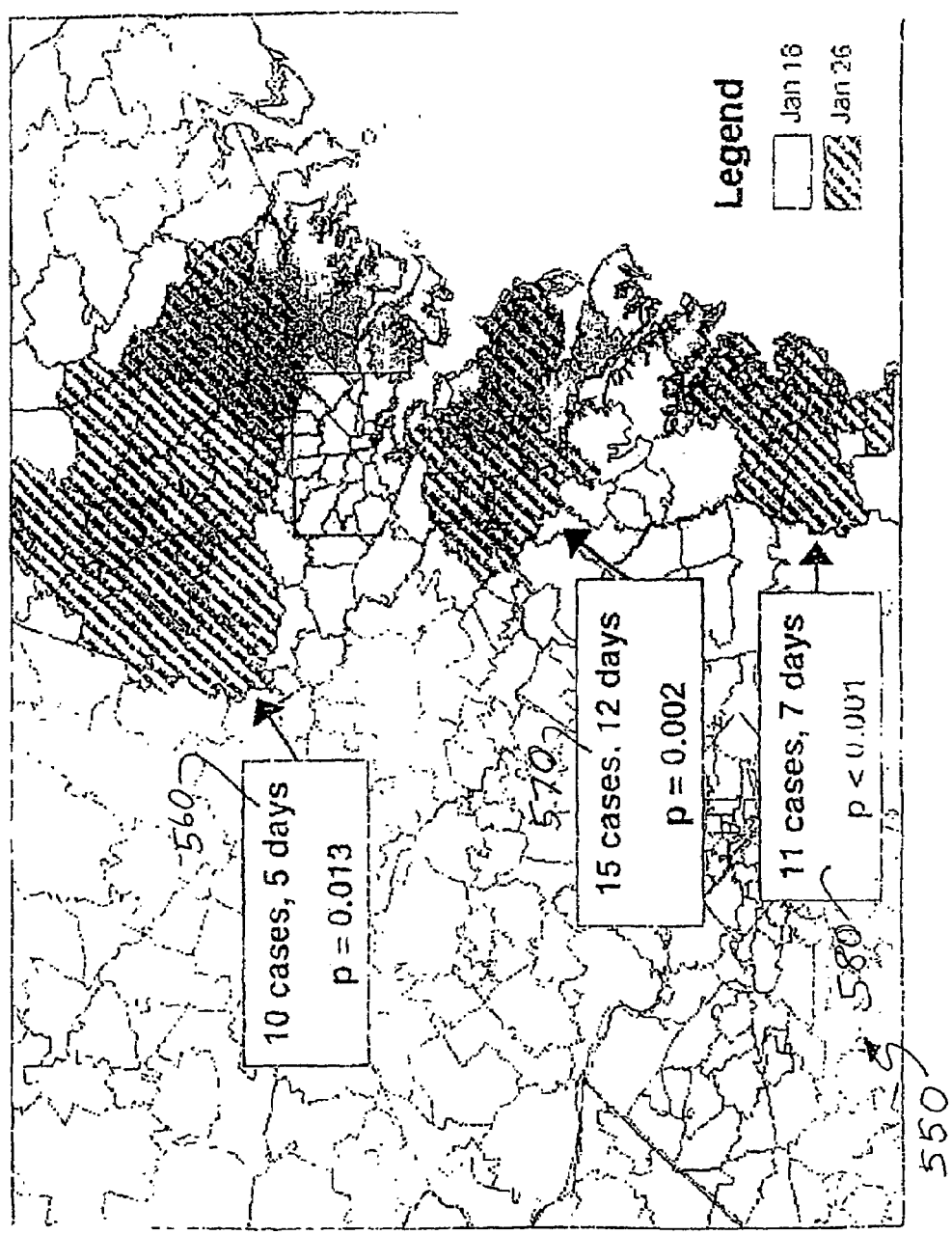
FIG. 5B is a graph that illustrates an example outbreak detection resulting from applying the method of FIG. 1A at a later date during the time series.

FIG. 5B is a graph 550 that illustrates an example outbreak detection resulting from applying the method of FIG. 1A at a later date during the time series. Graph 550 shows a map of the same sub-regions as shown in FIG. 5A but as of Jan. 26, 2001. Three areas with significant outbreaks are detected as of Jan. 26, 2001. One outbreak, indicated by box 560, is associated with 10 cases in 5 days; another outbreak, indicated by box 570, is associated with 15 cases in 12 days; another outbreak, indicated by box 580, is associated with 11 cases in 7 days. The probability that such outbreaks would be caused by random errors of normal variability is less than 0.001 for box 580, about 0.002 for box 570, and about 0.013 for box 560; thus the outbreaks are significant.

7. Hardware Overview

Figure 6:
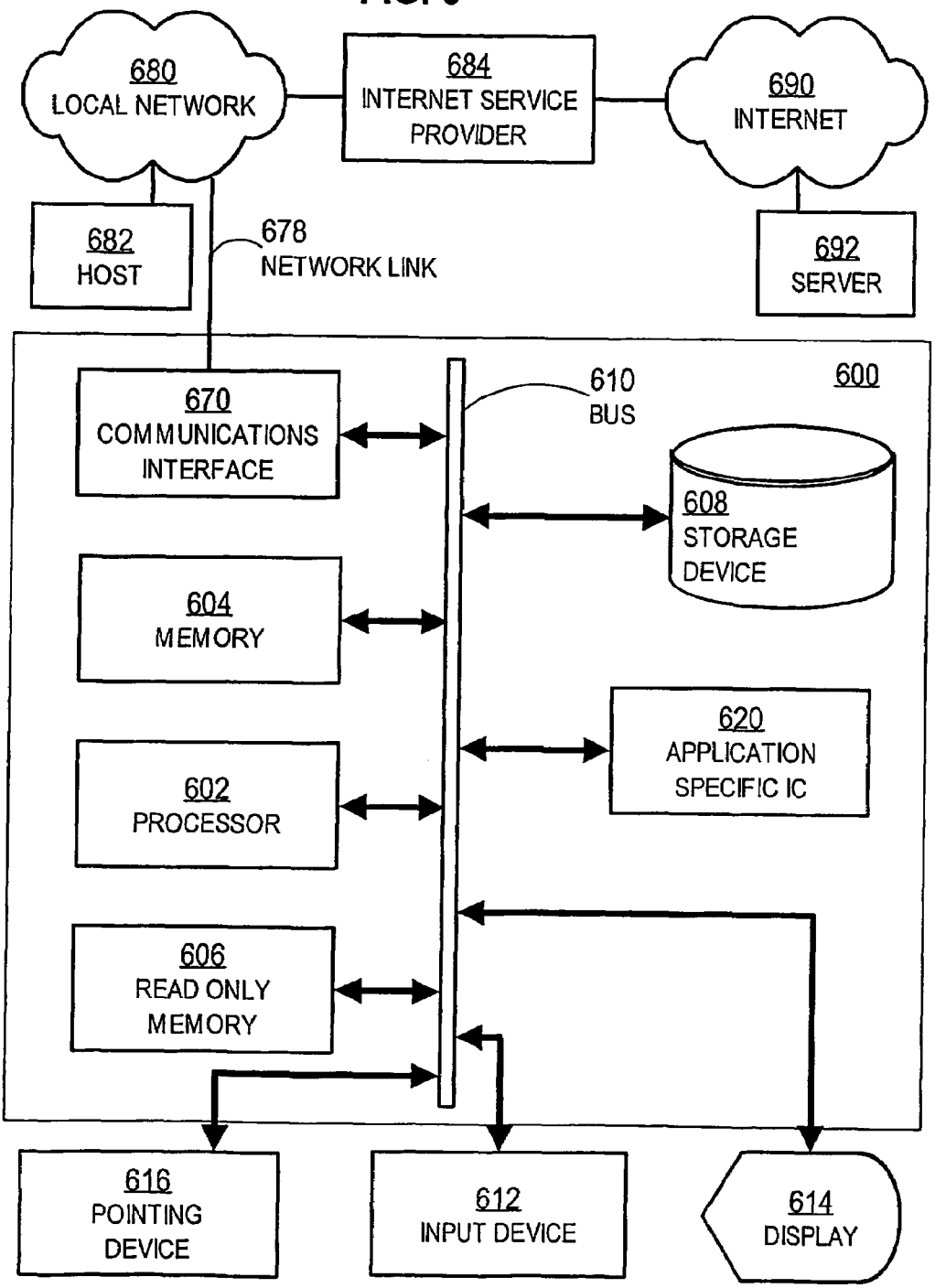
FIG. 6 is a block diagram that illustrates a computer system upon which an embodiment of the invention may be implemented.

FIG. 6 is a block diagram that illustrates a computer system 600 upon which an embodiment of the invention may be implemented. Computer system 600 includes a communication mechanism such as a bus 610 for passing information between other internal and external components of the computer system 600. Information is represented as physical signals of a measurable phenomenon, typically electric voltages, but including, in other embodiments, such phenomena as magnetic, electromagnetic, pressure, chemical, molecular and atomic interactions. For example, north and south magnetic fields, or a zero and non-zero zero electric voltage, represent two states (0, 1) of a binary digit (bit). A sequence of binary digits constitutes digital data that is used to represent a number or code for a character. A bus 610 includes many parallel conductors of information so that information is transferred quickly among devices coupled to the bus 610. One or more processors 602 for processing information are coupled with the bus 610. A processor 602 performs a set of operations on information. The set of operations include bringing information in from the bus 610 and placing information on the bus 610. The set of operations also typically include comparing two or more units of information, shifting positions of units of information, and combining two or more units of information, such as by addition or multiplication. A sequence of operations to be executed by the processor 602 constitute computer instructions.

Computer system 600 also includes a memory 604 coupled to bus 610. The memory 604, such as a random access memory (RAM) or other dynamic storage device, stores information including computer instructions. Dynamic memory allows information stored therein to be changed by the computer system 600. RAM allows a unit of information stored at a location called a memory address to be stored and retrieved independently of information at neighboring addresses. The memory 604 is also used by the processor 602 to store temporary values during execution of computer instructions. The computer system 600 also includes a read only memory (ROM) 606 or other static storage device coupled to the bus 610 for storing static information, including instructions, that is not changed by the computer system 600. Also coupled to bus 610 is a non-volatile (persistent) storage device 608, such as a magnetic disk or optical disk, for storing information, including instructions, that persists even when the computer system 600 is turned off or otherwise loses power.

Information, including instructions, is provided to the bus 610 for use by the processor from an external input device 612, such as a keyboard containing alphanumeric keys operated by a human user, or a sensor. A sensor detects conditions in its vicinity and transforms those detections into signals compatible with the signals used to represent information in computer system 600. Other external devices coupled to bus 610, used primarily for interacting with humans, include a display device 614, such as a cathode ray tube (CRT) or a liquid crystal display (LCD), for presenting images, and a pointing device 616, such as a mouse or a trackball or cursor direction keys, for controlling a position of a small cursor image presented on the display 614 and issuing commands associated with graphical elements presented on the display 614.

In the illustrated embodiment, special purpose hardware, such as an application specific integrated circuit (IC) 620, is coupled to bus 610. The special purpose hardware is configured to perform operations not performed by processor 602 quickly enough for special purposes. Examples of application specific ICs include graphics accelerator cards for generating images for display 614, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 600 also includes one or more instances of a communications interface 670 coupled to bus 610. Communication interface 670 provides a two-way communication coupling to a variety of external devices that operate with their own processors, such as printers, scanners and external disks. In general the coupling is with a network link 678 that is connected to a local network 680 to which a variety of external devices with their own processors are connected. For example, communication interface 670 may be a parallel port or a serial port or a universal serial bus (USB) port on a personal computer. In some embodiments, communications interface 670 is an integrated services digital network (ISDN) card or a digital subscriber line (DSL) card or a telephone modem that provides an information communication connection to a corresponding type of telephone line. In some embodiments, a communication interface 670 is a cable modem that converts signals on bus 610 into signals for a communication connection over a coaxial cable or into optical signals for a communication connection over a fiber optic cable. As another example, communications interface 670 may be a local area network (LAN) card to provide a data communication connection to a compatible LAN, such as Ethernet. Wireless links may also be implemented. For wireless links, the communications interface 670 sends and receives electrical, acoustic or electromagnetic signals, including infrared and optical signals, that carry information streams, such as digital data. Such signals are examples of carrier waves.

The term computer-readable medium is used herein to refer to any medium that participates in providing instructions to processor 602 for execution. Such a medium may take many forms, including, but not limited to, non-volatile media, volatile media and transmission media. Non-volatile media include, for example, optical or magnetic disks, such as storage device 608. Volatile media include, for example, dynamic memory 604. Transmission media include, for example, coaxial cables, copper wire, fiber optic cables, and waves that travel through space without wires or cables, such as acoustic waves and electromagnetic waves, including radio, optical and infrared waves. Signals that are transmitted over transmission media are herein called carrier waves.

Common forms of computer-readable media include, for example, a floppy disk, a flexible disk, a hard disk, a magnetic tape, or any other magnetic medium, a compact disk ROM (CD-ROM), or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 678 typically provides information communication through one or more networks to other devices that use or process the information. For example, network link 678 may provide a connection through local network 680 to a host computer 682 or to equipment 684 operated by an Internet Service Provider (ISP). ISP equipment 684 in turn provides data communication services through the public, world-wide packet-switching communication network of networks now commonly referred to as the Internet 690. A computer called a server 692 connected to the Internet provides a service in response to information received over the Internet. For example, server 692 provides information representing video data for presentation at display 614.

The invention is related to the use of computer system 600 for implementing the techniques described herein. According to one embodiment of the invention, those techniques are performed by computer system 600 in response to processor 602 executing one or more sequences of one or more instructions contained in memory 604. Such instructions, also called software and program code, may be read into memory 604 from another computer-readable medium such as storage device 608. Execution of the sequences of instructions contained in memory 604 causes processor 602 to perform the method steps described herein. In alternative embodiments, hardware, such as application specific integrated circuit 620, may be used in place of or in combination with software to implement the invention. Thus, embodiments of the invention are not limited to any specific combination of hardware and software.

The signals transmitted over network link 678 and other networks through communications interface 670, which carry information to and from computer system 600, are exemplary forms of carrier waves. Computer system 600 can send and receive information, including program code, through the networks 680, 690 among others, through network link 678 and communications interface 670. In an example using the Internet 690, a server 692 transmits program code for a particular application, requested by a message sent from computer 600, through Internet 690, ISP equipment 684, local network 680 and communications interface 670. The received code may be executed by processor 602 as it is received, or may be stored in storage device 608 or other non-volatile storage for later execution, or both. In this manner, computer system 600 may obtain application program code in the form of a carrier wave.

Various forms of computer readable media may be involved in carrying one or more sequence of instructions or data or both to processor 602 for execution. For example, instructions and data may initially be carried on a magnetic disk of a remote computer such as host 682. The remote computer loads the instructions and data into its dynamic memory and sends the instructions and data over a telephone line using a modem. A modem local to the computer system 600 receives the instructions and data on a telephone line and uses an infra-red transmitter to convert the instructions and data to an infra-red signal, a carrier wave serving as the network link 678. An infrared detector serving as communications interface 670 receives the instructions and data carried in the infrared signal and places information representing the instructions and data onto bus 610. Bus 610 carries the information to memory 604 from which processor 602 retrieves and executes the instructions using some of the data sent with the instructions. The instructions and data received in memory 604 may optionally be stored on storage device 608, either before or after execution by the processor 602.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A system for early detection of localized exposure to an agent active on a human population, comprising:
    a processor; and
    a computer readable medium carrying one or more sequences of instructions which,
        when executed by the processor, cause the processor to carry out the steps of:
        collecting, for each data type of a plurality of different data types relevant for detecting exposure to the agent, a plurality of time series of data at a corresponding plurality of locations associated with the data type,
            wherein each different data type is an indicator of human population health that may be affected by exposure to the agent;
        generating measures of anomalous conditions of human population health, each indicative of the localized exposure to the agent, at the plurality of locations for each of the plurality of different data types based on the plurality of time series and a temporal model for each data type;

performing cluster analysis on the measures of anomalous conditions to determine an estimated location and estimated spatial size of effects from the agent around the estimated location;

generating a replica of anomalous conditions, resulting from a hypothetical exposure to the agent, for a particular location within the estimated spatial size of effects determined during said step of performing cluster analysis by modeling a hypothetical exposure event that is based on at least one of the estimated location and the spatial size of the effects determined during said step of performing cluster analysis;

matching the replica to the measures of anomalous conditions for the particular location to determine whether the measures of anomalous conditions indicate an actual exposure event similar to the hypothetical exposure event;

producing at least one of a modified estimated location and a modified estimated spatial size or effects from the agent based on a result of said step of matching the replica;

generating a modified replica of anomalous conditions for a second particular location within the modified estimated spatial size by modeling a modified hypothetical exposure event that is based on at least one of the modified estimated location and the modified spatial size of the effects;

matching the replica to the measures of anomalous conditions for the second particular location to determine whether the measures of anomalous conditions indicate an actual exposure event similar to the modified hypothetical exposure event; and if it is determined an actual exposure event has occurred, then sending, via a computer interface, an alert signal that indicates a likely time, a likely location and a spatial size of the actual exposure.

2. the system of claim 1, wherein:

said step of generating measures of anomalous conditions further comprises determining a particular temporal model for a particular data type of the plurality of data types by performing auto-regression on a portion of a time series of data for the particular data type.

3. The system of claim 1, wherein:

said step of generating measures of anomalous conditions further comprises determining a particular temporal model for a particular data type of the plurality of data types by performing a cumulative summation process control analysis on a portion of a time series of data for the particular data type.

4. The system of claim 1, wherein:

said step of generating measures of anomalous conditions further comprises:

determining an expected value for a particular data type at a particular time based on a particular temporal model for the particular data type; and generating a measure of anomalous conditions based on the expected value and an actual value for the particular data type at the particular time; and said step of performing cluster analysis further comprises comparing a first ratio of the actual value for a first data type divided by the expected value for the first data type at a first location with a second ratio of the actual value for a second data type divided by the expected value for the second data type at a second location.

5. The system as recited in claim 1, wherein:

the first data type and the second data type are the same; and the first location and the second location are different.

6. The system as recited in claim 1, wherein the first data type and the second data type are different.

7. The system as recited in claim 4, wherein the data types include at least one of:

over the counter drug sales at a drug store;

absenteeism at a school;

number of medical insurance claim forms or physician office visits filed in an area;

and number of cases in categories of symptoms at a hospital or health clinic.

8. The system of claim 1, wherein said step of performing cluster analysis further comprises constructing a circle, having a radius representative of the spatial size, around the plurality of locations corresponding to the plurality of time series of data.

9. The system of claim 1, wherein the data types include at least one of:

over the counter drug sales at a drug store;

absenteeism at a school;

number of medical insurance claim forms or physician office visits flied in an area;

and number of cases in categories of symptoms at a hospital or health clinic.

* * * * *